United States Patent [19]

Pfannenstiel et al.

[11] Patent Number: 4,603,726

[45] Date of Patent: Aug. 5, 1986

[54] METHOD OF MAKING INDIVIDUAL CASTINGS

[75] Inventors: Hubert Pfannenstiel, Lenggries; Heinz-Joachim Hübner, Wörthsee, both of Fed. Rep. of Germany

[73] Assignee: ESPE Fabrik pharmazeutischer Präparate GmbH, Seefeld, Fed. Rep. of Germany

[21] Appl. No.: 549,190

[22] Filed: Nov. 4, 1983

[30] Foreign Application Priority Data

Nov. 5, 1982 [DE] Fed. Rep. of Germany ....... 3240907

[51] Int. Cl.⁴ .............................................. B22C 9/02
[52] U.S. Cl. ......................................... 164/35; 164/45
[58] Field of Search ...................... 164/34, 35, 36, 44, 164/45

[56] References Cited

U.S. PATENT DOCUMENTS

Re. 28,789  4/1976  Chang ................................. 430/271
2,691,197 10/1954  McFadden et al. .................. 164/35
3,798,134  3/1974  Hynes ................................. 264/227

*Primary Examiner*—Nicholas P. Godici
*Attorney, Agent, or Firm*—Becker & Becker, Inc.

[57] ABSTRACT

A method of making individual castings. In the production of individual castings, in particular in dental engineering, the casting is usually premodeled in wax. However, this casting model is very susceptible to deformation, which leads to inaccuracies in the fit of the casting. With the present method, at least a part of the casting model is built up from a photopolymerizable compound which burns leaving no residue. Advantageously, the curing is carried out, in the presence of a suitable initiator, with visible light; the basis of the compound is a photopolymerizable (meth)acrylic acid ester. In dental engineering, with the present method there is made possible in a simple manner to build up form-stable casting models for making crowns, bridges, and inlays and, particularly favorably, complicated secondary parts for removable dental appliances.

1 Claim, No Drawings

METHOD OF MAKING INDIVIDUAL CASTINGS

BACKGROUND OF THE INVENTION

1. Field of the Invention

The present invention relates to a method of making individual castings, for example in the field of dental engineering or jewelry production.

2. Description of the Prior Art

To make prosthetic metal structures in dental engineering, e.g. crowns, inlays or bridges, up to now the latter are first modeled in wax, as a result of which they are provided with the appropriate individual shape. A prefabricated sprue is secured to this so-called casting pattern or model; thereafter, the casting model is enveloped in a refractory embedding compound. The wax composition is then removed either by boiling out with hot water, or by burning the wax at temperatures between about 500° and 700° C. Molten metal is then introduced into the resulting negative mold, is allowed to cool, and is removed from the mold, so that a casting having the same shape as the wax casting model is thus obtained.

It is obvious and readily apparent that with regard to its accuracy of fit in the corresponding situation in the mouth, the casting is only as good as the wax casting model. Generally, the dental technician has a jaw model, for example of plaster, to which he adapts the casting model. However, when the parts modeled in wax are removed from the model, there is a great danger that the casting model becomes distorted and that therefore the metal casting finally obtained does not fit. Moreover, during the modeling, the wax must be liquefied by heating, so that, particularly with large bridge structures, strong thermal stresses arise which can lead to a distortion or breaking of the casting model. Also, due to nonuniform temperatures, different wax consistencies are obtained, so that the uniformity of the wax application is not always ensured, and the modeling as a whole is made difficult. An additional danger is the formation of streaks and bubbles.

To avoid deformation of the wax when it is removed from the model, a procedure has been adopted in which caps of plastic deep-draw foil are made over crown stumps. However, there is again a danger of deformation due to the subsequent thermal stress during the application of the molten wax. The situation is particularly difficult in the case of multi-part removable structures, e.g. conical crowns, telescopic crowns, or double crowns for interlocking. These structures consist fundamentally of a metal crown, which is referred to as the primary part and is securable to the tooth stump, and over which a so-called secondary crown is made in exact fit. Prostheses or bridges are subsequently secured to this secondary part, and are thus removable. A requirement for the fulfillment of the holding function of secondary parts on primary parts is an exactly fitting production of the secondary crown on the primary crown. The same applies to attachment, lock and bar structures. Since it is very difficult to model these inter-engaging parts from wax, to increase the stability particularly the secondary parts of these detachable prostheses are modeled with self-polymerizing methyl methacrylate, at least to a certain layer thickness. Such a procedure is described in "Quintessenz" 1965, No. 6, pages 57 and 58.

These compounds, which usually cure on the principle of redox polymerization, have, however, a relatively short working time, yet require a relatively long time until they are completely polymerized. Due to the high temperature peak during the curing, thermal stresses easily occur; in addition, bubbles can form easily at the surface. There is further necessary, because of the high polymerization shrinkage, to apply great amounts of the compound, and to grind it back to the final size. This fact prevents an exact anatomical modeling in the build-up method, and therefore makes it extremely complicated and time-consuming. This is also because the polymerization starts immediately after the mixing of the compound, and the consistency of the compound changes continuously during the work. At the start of the work, the methyl methacrylate preparation remains liquid for a relatively long time, so that the parts which are not to be covered must be protected from overflow in complicated manner, e.g. by a wax ring, from overflow. Working with these polymers is thus a very complicated and involved procedure which moreover results in excessively high material consumption.

An object of the present invention therefore is to provide a method which permits the simple production of exactly fitting casting models, even in the case of very difficult structures, in particular in dental engineering.

This object, and other objects and advantages of the present invention, will appear more clearly from the following specification in conjunction with the accompanying Examples.

SUMMARY OF THE INVENTION

The method of the present invention is characterized primarily in that the casting model is built up at least partially by photopolymerization of a photopolymerizable compound. Thereafter, at least one sprue is secured to the casting model, the casting model is embedded in a refractory molding compound, the casting model is removed without residue by heating, molten metal is introduced into the mold obtained, the mold is allowed to cool, and the casting is removed from the mold.

German Offenlegungsschrift No. 2 910 077 describes the production of dental prostheses by photopolymerization of plastics. No reference is made anywhere as to the production of casting models for casting work.

To carry out the method according to the present invention, a rapidly photopolymerizable substance is used together with a photoinitiator. It is obvious that the plastic formed from these preparations by photopolymerization must be removable without residue, e.g. by burning.

Suitable as photopolymerizable compounds are the esters of acrylic acid and methacrylic acid. Di- and polyfunctional (meth) acrylic acid esters lead to particularly deformation-resistant casting models. However, mixtures of polythiols and polyallyl compounds may also be used in stoichiometric relationship in accordance with U.S. Pat. No. 3,898,349—Kehr et al dated Aug. 5, 1975, entitled "Polyene/Polythiol Paint Vehicle" for coating a substrate (W. R. Grace & Co.).

The known photoinitiators may be used, e.g. benzophenones, benzoin ethers, benzil ketals, thioxanthones, and aromatic or aliphatic diketones. Particularly suitable are 1,2-diketones, in particular camphor quinone and phenanthrenequinone.

In addition, so-called photoactivators can be used, e.g. organic phosphites or amines. In the case of 1,2- diketones, tertiary amines are particularly effective activators.

To increase the mechanical strength, reduce the polymerization shrinkage, and to control the viscosity, the preparations for carrying out the inventive method may also contain organic fillers and/or soluble organic plastics. Suitable are, for example, polymethyl methacrylate, nylon beads, polyvinyl acetate, polyvinyl chloride, or polystyrene. However, there must be ensured that the additives chosen burn without residue or are melted out under heat.

The viscosity of the inventive compound is adjusted in a favorable manner by the aforementioned steps, so that the composition can be applied finely with a brush or a spatula, but without the action of shearing forces has only a low flowability.

For improved distinction from the jaw model, and for checking the thickness of the layer applied, it is advantageous to provide the photopolymerizable compound, used with pigments and/or opacifying agents, especially organic pigments and/or opacifying agents. The compound can be worked in particularly favorable manner if it has a low transparency because the layer thickness applied can then be visually checked by the operator with the aid of the degree of opacity. Again, there is important that the additives chosen can be removed without residue.

The wavelength of the light used in the photopolymerization of the preparations described must be selected such that it corresponds to the active light absorption of the photoinitiator. Because of the harmlessness of the radiation, and the simple and economic construction of the irradiation unit, there is advantageous to use visible light in the wavelength range of about 400–500 nm, preferably together with 1,2-diketone initiators.

Of course, the shorter-wave radiation ranges can also be used if suitable protective measures are adopted.

The compounds, which in addition may also contain the usual stabilizers and inhibitors, are kept ready for use in light-tight containers.

According to the method of the present invention, the photopolymerizable compounds described above can partially or completely replace the wax in the production of casting models. The light-curing material is applied with a brush in a thin layer to the tooth stump or to the corresponding primary part, this layer is then cured in a few seconds or minutes by exposure with the appropriate light. According to this method, a form-stable base of photopolymerized plastic can be made, and the further build-up is then done as usual with wax. Alternatively, by stepwise building up in thin layers, each of which is individually subjected to the light curing, the entire wax may be replaced by the photopolymer. Because the layers, under the action of light, are cured immediately to form a hard, form-stable plastic, a distortion or flowing away of the material is not possible. Possibly, prior to using the photopolymerizable plastic, the plaster model or the primary part must be covered with a suitable insulating agent (e.g. silicone).

Because of the long working time in the absence of an intense light source, application in small portions, and efficient modeling of the corresponding parts, are possible. This eliminates complicated or expensive correction work by grinding or the like. A complicated covering, of the parts, which are not to come into contact with the material, for example covering thereof with wax, is not necessary because rapid fixing and stabilizing of the compound applied are possible. The stable polymer permits a detachment of the casting models in the half-finished condition as well, for example to check the inner surfaces. Furthermore, as a result of the application and fixing in small portions, excessive heating and resultant bubble formation or streaking can be avoided reliably. Since the modeling material is cured by directed and controllable irradiation, a particularly careful and economic working with the compounds is possible; there is no need to throw away large quantities of excessive material, because only the amount of material required is taken from the package. The application in thin layers also largely compensates for the polymerization shrinkage. After the application of each layer, curing is effected by exposing to an intense light source.

After completion of the casting model by irradiation of the photopolymerizable compound, and possibly further amplification with wax, a sprue is applied in the usual manner. To facilitate removal of the casting model obtained, by melting out and/or burning, it may be advantageous to provide further sprues on the casting model in addition to the main sprue. The casting model is then enclosed in an embedding compound. At a temperature of about 500°–700° C., the casting model is removed to leave no residue by melting out and/or burning, and thereafter molten metal is introduced as usual.

The securing of parts which are to be soldered, such as crowns, bridges, or clasps or braces, is also possible with light-curing or photopolymerizable material instead of adhesive wax. The securing takes place after fixing of the parts on the model by photopolymerization. Thereafter, as usual, a partial enclosing in soldering embedding compound is carried out, the plastic is burned off the metal, and the soldering is done.

To recapitulate, one can build up as a dental casting model in dental engineering such items including a crown, an inlay, a bridge, the secondary part of a conical crown, telescopic crown, double crown, or a male part for individual attachments, as well as a telescoping anchor, bar attachment, or soldering connection.

The method according to the present invention will be explained in detail subsequently with the aid of examples in dental engineering. However, the inventive method is not restricted to dental engineering, but can be used in all cases where high-quality individual castings of relatively small dimensions are to be made. Possible uses are, therefore, for example, also for individual castings for high-quality machines, in the manufacture of jewelery, and in orthopedic prostheses, e.g. for castings for filling bone defects.

EXAMPLE 1

(Production of an inlay)

The positive model stump of the prepared cavity is first treated with an insulating solution on an alginate basis. A mixture of 4 parts by weight bis-GMA (reaction product of bisphenol A and 2 equivalents glydicyl methacrylate), and 1 part by weight triglycol dimethacrylate, initiated with 0.2 percent camphor quinone and 1.5 percent triethanol amine, is applied with a brush in thin layers, each of which is subsequently irradiated for 10 seconds using a commercially available dental irradiation apparatus for visible light (Elipar, of the company ESPE). When completely modeled, the casting model is removed from the cavity, a prefabricated sprue of wax is secured thereto and thereupon embedding the same in a refractory compound. By heating to about 600° C., the casting model is burned free of any residue. Thereafter, in the usual manner, molten metal (gold alloy) is introduced into the mold obtained. After cooling, the casting is removed from the mold in the usual manner and is trimmed. An extremely accurately fitting gold cast inlay is obtained.

EXAMPLE 2

(Production of a crown)

The model stump is insulated with a conventional, moisture-vulcanizing silicone film. As described in example 1, by application of the photopolymerizable compound layer by layer, which compound, however, instead of triglycol dimethacrylate, contains bishydroxymethylbicyclo [5.2.1.0$^{2,6}$]—decane diacrylate, and by respective exposure thereof, a uniform cap of about 0.5 mm wall thickness is formed over the stump. The cured cap is to be removed from the stump without deformation, e.g. for checking the inner surfaces or the edges.

The crown can now be modeled onto the cap in the usual manner with wax or, in accordance with example 1, by application and exposure of layers of the light-curing compound. Thereafter, in the usual manner, a sprue is provided, the embedding is carried out, the plastic and wax are burned at about 600° C., and the casting is performed. An exactly fitting crown is obtained.

EXAMPLE 3

(Production of a bridge)

To produce a bridge, the model stumps are insulated in the usual manner, and as described in example 2 are covered with a cap of light-cured plastic of 0.5 mm wall thickness. In this case, the photoinitiator is benzil and not camphor quinone. The caps of the individual stumps are now connected to a stabilizing frame by application of the photopolymerizable plastic and exposure; the further build-up can now again be as usual with wax, or with photopolymerizable compound. The further casting is carried out in the usual manner. The bridge obtained is free from stress and fits exactly onto the model.

EXAMPLE 4

(Production of the secondary part of a conical crown)

To produce a removable bridge having a conical crown, in the usual manner, the finished primary crown milled in metal is removed from the tooth stump and is enclosed, as in example 2, on the outer surface with a uniform layer of about 0.5 mm of the light-curing material. After the irradiation, the plastic cap can be removed from the primary crown to check the inside. After the checking, the exactly fitting sleeve as formed is placed again on the primary part, and the anatomical form of the secondary crown is either modeled in wax, or is built up by gradual application in portions and curing of the light-curing plastic.

The modeled and cured secondary crown is then removed from the primary crown, and as usual is provided with a sprueformer of wax and is surrounded with refractory embedding compound. By heating to about 700° C., the wax and light-curing plastic are burned free of residue. The casting, removing from the mold, and trimming are then carried out in the usual manner. A secondary crown of metal is obtained which is identical in form and accuracy of fitting to the secondary crown of light-curing material, and has good conical bonding to the primary crown.

There is possible, in a similar manner, to also make the secondary parts of telescopic crowns and double crowns, including the lock elements (e.g. rotary, pivot and plug locks).

EXAMPLE 5

(Production of male parts for individual attachments)

The recess, milled in dovetail shape, of a full-cast crown (female) is filled with a mixture of 7 parts by weight of the reaction product of 2,2,4-trimethylhexamethylene diisocyanate and 2 equivalents hydroxyethyl methacrylate, with 1 part by weight triglycol dimethacrylate which contains 0.2% camphor quinone and 1% methyldiethanol amine, and is cured by a 40-second exposure to a dental irradiation unit. Thereafter, the outer form of the male part is built up in layers as described in example 2. After the curing, the part of light-cured material is removed from the female part. The resulting male part is then cast as usual. A male part is obtained which fits without any problems into the milled female part.

Since individual attachments are frequently used in conjunction with crowns and bridges, which carry both the female and the male parts, there is possible to form the male parts in wax on the crowns modeled in wax, and to cast them therewith.

Of course, male parts for individual attachments may also be made by the inventive method on veneer crowns and bridges of metal; the recesses may also be T-groove-shaped or channel-shaped. The male parts obtained in metal have a very accurate fit, and completely fulfill their retaining function by friction, and their function as guides during removal and insertion.

EXAMPLE 6

(Production of a telescoping anchor)

In the case of a telescoping anchor as well, the secondary part is guided and held on the primary part by sliding friction, so as to have a very accurate fit. However, only a part and not all of the outer surface of the primary crown is milled and used as function surface. The remainder of the primary crown is either left in its anatomical form in metal, or alternatively, after appropriate shaping, is provided with a veneer or facing material. In the milled portion of the primary crown, grooves and shoulders are milled and serve to guide and support the secondary part on the primary part. There is particularly difficult to reproduce exactly these grooves and shoulders in the secondary part; moreover, the unmilled portion of the secondary crown must not come into contact with the casting model material.

Analagous to example 4, the secondary crown is built up from the light-curing compound in layers on the milled outer surface of the primary crown, and after application of each layer is cured by irradiation. This procedure makes it unnecessary to mask the unmilled portions which are not to be covered with plastic (e.g. with wax). In this manner, a stress-free secondary part is obtained which is made without streak formation at the surface. Thereafter, embedding is carried out in the usual manner, the casting model is burned at 700° C., and the casting is then effected. Thus, in a simple manner, an accurately fitting telescoping anchor is obtained.

In a similar manner, there is also possible to make a bar die or attachment (in this case the secondary part) over the primary part (a bar counter-die).

EXAMPLE 7

(Preparatory connection for soldering)

A bridge and the associated clasp are placed on the plaster model, where the bridge and clasp are joined together by application of the photopolymerizable plastic and subsequent curing by irradiation. Thereafter, the combination is removed from the model, is partially enclosed with a refractory compound, and is thus further fixed in position. In the usual manner, after the curing of the soldering embedding compound, the photocured plastic is burned off the metal parts; thereafter, soldering is carried out in the usual manner. The composite structure thus obtained fits extremely accurately on the model.

The present invention is, of course, in no way restricted to the specific disclosure of the specification and Examples, but also encompasses any modifications within the scope of the appended claims.

What we claim is:

1. In a method of making relatively small individual independent metal dental castings that are three-dimensional in configuration by building up, in the field of dental engineering, including a positive model of a crown, an inlay, a bridge, the secondary part of a conical crown, telescopic crown, double crown, or a male part for individual attachments, as well as a telescoping anchor, bar attachment, or soldering connection, said method having the improvement therewith comprising steps of:

building up a dental casting model at least partially by photopolymerizing a photopolymerizable compound for hardening in combination therewith;

applying said photopolymerizable compound in a plurality of layers, and individually subjecting each layer to photocuring using visable light in the wave length range of 400–500 nm;

thereafter securing at least one sprue to said casting model;

embedding said dental casting model in a refractory molding compound;

heating said refractory molding compound and said embedded dental casting model to a temperature of 500°–700° C. to melt and/or burn out said dental casting model, free of residue, from said molding compound and to form a mold therein;

introducing molten metal into said mold to form a specific dental casting;

cooling said mold and casting; and finally removing said dental casting from said mold;

said photopolymerizable compound contains one of the compounds selected from the group consisting of acrylic acid ester and methacrylic acid ester.

* * * * *